United States Patent [19]

Johnson-Wood et al.

[11] Patent Number: 5,422,244

[45] Date of Patent: Jun. 6, 1995

[54] DETECTION OF BRAIN α1-ANTICHYMOTRYPSIN

[75] Inventors: Kelly Johnson-Wood, Belmont; Dale Schenk, Pacifica, both of Calif.

[73] Assignee: Athena Neurosciences, Inc., South San Francisco, Calif.

[21] Appl. No.: 880,216

[22] Filed: May 5, 1992

[51] Int. Cl.$^6$ ........................................... G01N 33/543
[52] U.S. Cl. ..................................... 435/7.1; 435/7.92; 435/7.94; 435/971; 436/518; 436/536; 436/811; 436/827
[58] Field of Search ....................... 435/7.1, 7.92, 7.94, 435/967, 971; 436/518, 536, 827, 811; 530/395, 396

[56] References Cited

U.S. PATENT DOCUMENTS 5,008,242  4/1991  Lezdey et al. ........................... 514/8

FOREIGN PATENT DOCUMENTS 0166623  1/1986  European Pat. Off. .
0441470  8/1991  European Pat. Off. .

OTHER PUBLICATIONS

Slifkin et al. "Lectins and Their Application to Clinical Microbiology", Clin. Microbiol. Rev. 3(3): 197–218 (Jul. 1990).
Matsubara et al, "α1-Antichymotrypsin as a Possible Biochemical Marker for Alzeheimer-Type Dementia", Ann. Neurol., 28: 561–567 (Oct. 1990).
Travis et al, "Human α-1-Antichymotrypsin: Purification and Properties", Biochem. 17(26): 5647–5651 (1978).
Sevier et al. "Monoclonal Antibodies in Clinical Immunology", Clin. Chem., 27(11): 1797–1806 (Nov. 1981).
Abraham et al. (1988), *Cell* 52:487–501.
Abraham and Potter (1989), *Ann. Med.* 21:77–81.
Baumann et al. (1991), *J. Mol. Biol.* 218:595–606.
Berninger (1986), *J. Med.* 16:101–128.
Hachulla et al. (1992), *Clinical Science* 82:439–446.
Kelsey et al. (1988), *J. Med. Genet.* 25:361–368.
Koo et al. (1991), *Neurobiology of Aging* 12:495–501.
Laine et al. (1991), *Eur. J. Biochem.* 197:209–215.
Laine and Hayem (1981), *Biochem. et Biophys. Acta* 668:429–438.
Lindmark et al. (1989), *Biochim. et Biophys. Acta* 997:90–95.
Mast et al. (1991), *Biochemistry* 30:1723–1730.
Morii and Travis (1983), *Biochem. Biophys. Res. Commun.* 111:438–443.
Nelson and Siman (1990), *J. Biol Chem.* 265:3836–3843.
Pasternack et al. (1989), *Am. J. Pathol.* 135:827–834.
Potempa et al. (1991), *J. Biol. Chem.* 266:21482–21487.
Richards et al (1991), *EMBO J.* 10:297–303.
Rubin et al. (1990), *J. Biol. Chem.* 265:1199–1207.
Travis and Morii (1981), *Meth. Enzymol.* 80:765–771.
Wick et al. (1987), *Virchows Archiv A* 411:23–32.

*Primary Examiner*—Carol E. Bidwell

[57] ABSTRACT

The present invention is related generally to methods and compositions for identifying and quantitating particular α1-antichymotrypsin species in a biological sample. More particularly, the present invention is related to methods and compositions for detecting and measuring a brain α1-antichymotrypsin species that is produced in brain tissue of individuals having a neuropathological condition and which is detectable in accessible biological samples. The invention provides detection assays, such as sandwich binding assays, for detecting and quantitating brain α1-antichymotrypsin in a biological sample, such as blood, urine, cerebrospinal fluid, or tissue. These detection assays are useful for detecting and diagnosing neuropathological diseases and for identifying cells of a human central nervous system lineage, and for other medical applications. The invention also provides binding components, such as antibodies that bind to brain α1-antichymotrypsin, and which have potential therapeutic and diagnostic medical imaging applications.

26 Claims, 1 Drawing Sheet

SEQUENCE LISTING ( 1 ) GENERAL INFORMATION:

(iii) NUMBER OF SEQUENCES: 4

( 2 ) INFORMATION FOR SEQ ID NO:1:

(i) SEQUENCE CHARACTERISTICS:
  (A) LENGTH: 5 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:1:

His Pro Asn Ser Pro
1               5

(2) INFORMATION FOR SEQ ID NO:2:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Region
    (B) LOCATION: 1..3
    (D) OTHER INFORMATION: /note="Residue #Microsoft Corp residues #Microsoft Corp (xi) SEQUENCE DESCRIPTION: SEQ ID NO:2:

Xaa Xaa Xaa Pro
1

(2) INFORMATION FOR SEQ ID NO:3:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 3..4
    (D) OTHER INFORMATION: /note="Xaa is any amino acid."

(xi) SEQUENCE DESCRIPTION: SEQ ID NO:3:

Ser Gly Xaa Gly
1

(2) INFORMATION FOR SEQ ID NO:4:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 3..4
    (D) OTHER INFORMATION: /note="Xaa is any amino acid."

(xi) SEQUENCE DESCRIPTION: SEQ ID NO:4:

His Pro Xaa Ser Pro Leu Asp Glu Glu Asn Leu Thr Gln Glu Asn
1               5                   10                  15

DETECTION OF BRAIN α1-ANTICHYMOTRYPSIN

TECHNICAL FIELD

The present invention is related generally to methods and compositions for identifying and quantitating particular α1-antichymotrypsin species in a biological sample. More particularly, the present invention is related to methods and compositions for detecting and measuring a brain α1-antichymotrypsin species that is produced in the brain tissue of individuals having a neuropathological condition and which is detectable in accessible biological samples.

BACKGROUND

Alzheimer's disease (AD) causes dementia in many elderly individuals and in individuals with Down's syndrome who survive to age 50. AD is characterized by several distinct pathological features that are visible on histological examination: large numbers of amyloid plaques surrounded by neurons containing neurofibrillary tangles and neuronal cell loss.

One hypothesis regarding the pathogenesis of the disease is that deposition of amyloid β polypeptide (βAP), which is the major macromolecular component of amyloid plaques, is the causative agent of the characteristic AD pathological changes leading to formation of neurofibrillary tangles, neuronal cell loss, vascular damage, and, ultimately, dementia (Hardy and Higgins (1992) Science 256: 184). Amyloid precursor protein (APP) is encoded by a single gene in humans. RNA transcripts of the APP gene are alternatively spliced to encode several APP protein isoforms; the predominant APP isoform in brain lacks a serine protease inhibitor domain that is present in other tissues. βAP is a proteolytic cleavage product arising from the carboxy region of various APP isoforms, including the predominant APP isoform in the brain (Kitaguchi et al. (1988) Nature 331: 530; Ponte et al., ibid., p.525; R. E. Tanzi, ibid., p.528; Kang and Muller-Hill (1990) Biochem. Biophys. Res. Commun. 166: 1192; Yoshioka et al. (1991) Biochem. Biophys. Res. Commun. 178: 1141; Johnson et al. (1990) Science 248: 854; Neve et al. (1990) Neuron 5: 329). According to this hypothesis, amyloidogenic βAP might be generated by one or more alternate proteolytic cleavage pathways. The accumulation of extracellular βAP results in insoluble amyloid deposits and may be neurotoxic, leading to neuronal death and neurofibrillary tangle formation.

The serine protease inhibitor (i.e., serine antiproteinase) alpha 1-antichymotrypsin (α1-ACT), which binds to chymotrypsin-like enzymes in a covalent manner, has been shown recently to be both a normal constituent of brain and an integral component of the amyloid neuritic plaques that form in Down's syndrome and AD (Abraham and Potter (1989) Ann. Med. 21: 77; Abraham et al. (1988) Cell 52: 487; Pasternack et al. (1989) Am. J. Pathol. 135: 827; Matsubara et al. (1990) Ann. Neurol. 28: 561; Koo et al. (1991) Neurobiology of Aging 12: 495). Since the neuritic plaques which characterize AD comprise βAP, which is presumably a proteolytic cleavage product of one or more APP isoforms (such as the major brain isoform which lacks a serine protease inhibitor domain), the presence of α1-ACT in amyloid plaques suggests that it may play a role in either normal or pathological proteolytic processing of APP isoforms.

Serine antiproteinases, also termed serpins, encompass a supergene family of proteinase inhibitors that regulate many of the serine proteases involved in inflammation and homeostasis. Alpha 1-antichymotrypsin belongs to the serpin supergene family that includes α1-antitrypsin (α1-AT), antithrombin III (ATIII), ovalbumin, angiotensinogen, human leuserpin 2 (hLS2), protein C inhibitor (plasminogen activator inhibitor III), rat kallikrein binding protein (RKBP), mouse contrapsin, and several other related proteins (e.g., murine Spi-2 genes).

The human serine protease inhibitor genes α1-AT and α1-ACT are acute-phase proteins which are induced in response to inflammation. These inhibitors function to limit the activity of specific serine proteases in vivo; α1-AT acts as an inhibitor of neutrophil elastase to protect the elastin fibers of the lung. The physiologic role of α1-ACT is not clearly defined but it likely functions in modulating the enzymatic activity of one or more specific serine protease(s). Human α1-ACT is a plasma protease inhibitor that specifically inactivates serine proteases of the chymotrypsin class, including cathepsin G and other proteases found in neutrophils, basophils, and tissue mast cells. Human α1-ACT is produced in liver, and it possesses the unusual feature of being a primary acute-phase protein whose plasma concentration may rise several-fold within 24 hours after tissue damage. These facts suggest that the primary role of α1-ACT is in regulating chymotrypsin-like enzymes, particularly those released during inflammatory episodes.

Human α1-ACT has been cloned, sequenced, and expressed in *E. coli* (Rubin et al. (1990) *J. Biol. Chem.* 26.5: 1199; Kelsey et al. (1988) *J. Med. Genet.* 25: 361). The human α1-ACT gene is approximately 12 kilobases (kb) in length and contains five exons and four introns (Bao et al. (1987) *Biochemistry* 26: 7755; Ragg and Preibisch (1988) *J. Biol. Chem.* 263: 12129). The human α1-ACT gene maps to the same region, q31-32.3 of chromosome 14, that the human α1-AT gene maps to (Rabin et al. (1986) *Somat. Cell Mol. Genet.* 12: 209) and the two genes are located within about 220 kb of each other (Sefton et al. (1990) *Genomics* 7: 382).

The homologous organization of genes of the serpin supergene family (Chai et al. (1991) *J. Biol. Chem.* 266: 16029; Meijers and Chung (1991) 266: 15028), the high degree of sequence homology between their protein sequences (Chandra et al. (1983) *Biochemistry* 22: 5055; Chao et al. (1990) *J. Biol. Chem.* 265: 16394; Suzuki et al. (1990) *J. Biochem.* 108: 344), and clustering of serpin genes at particular chromosal locations (Rabin et al. (1986) op.cit.; Sefton et al. (1990) op.cit.) suggests that these genes arose by recent gene duplication events (Bao et al. (1987) op.cit.).

Human α1-ACT are glycoproteins encoded by the single copy α1-ACT gene, which are typically about 68,000 daltons and comprise about 25–35% carbohydrate. α1-ACT is found in whole blood, serum, plasma, cerebrospinal fluid (CSF), and brain tissue. The predominant plasma form of α1-ACT is presumed to be synthesized in the liver. Proteolytically modified α1-ACT has been crystallized, and Asn70 and Asn104 have been identified as putative glycosylation sites (Baumann et al. (1991) *J. Mol. Biol.* 218: 595).

Two predominant isoforms of α1-ACT have been identified in plasma and correspond to a microheterogeneity at the amino-terminus of α1-ACT that can be identified by the presence of two well-separated components of about 68 kD on immunoelectrophoresis (Travis et al. (1978) *Biochemistry* 17: 5647). Most investigators report that the major isoform has an amino-terminal arginine (Travis (1978) op.cit.; Laine and Hayem (1981) *Biochim. Biophys. Acta* 6.68.: 429). However, one report, Morii and Travis (1983) *Biochem. Biophys. Res. Commun.* 111: 438, found that over 90 percent of α1-ACT has an amino-terminal aspartic acid and less than 10 percent has an amino-terminal arginine, with a fifteen amino acid peptide fragment being cleaved off the amino-terminus of the major isoform (N-terminal aspartic acid) to yield the minor form (N-terminal arginine). A more recent report, Lindmark et al. (1989) *Biochim. Biophys. Acta* 997: 90, indicates that one α1-ACT ACT isoform has the amino-terminal sequence (His-Pro-Asn-Ser-Pro-(SEQ. ID. NO:1)) and the other isoform is truncated by two residues and has the amino-terminal sequence (Asn-Ser-Pro). α1-ACT purified from normal human serum has also been separated by affinity chromatography on a Concanavalin-A-Sepharose column into three microheterogenous forms that differ by their N-linked carbohydrate structures (Laine et al. (1991) *Eur. J. Biochem.* 197: 209). Hence, there appear to be several discrete forms of α1-ACT in human plasma.

Immunocytochemical staining has identified one or more proteins in amyloid deposits in AD neuritic plaques that are reactive with antibodies to α1-ACT. In situ hybridization studies using probes corresponding to an α1-ACT cDNA isolated from a liver cDNA library have identified astrocytes as a source of mRNA that hybridizes to α1-ACT cDNA probes, with astrocytes surrounding neuritic plaque cores having intense labeling by the probe (Pasternack (1989) op.cit.; Koo et al. (1991) op.cit.). The levels of mRNA that hybridize to a liver α1-ACT cDNA in brain gray matter has been shown to be elevated in AD brain versus control brain (Abraham (1988) op.cit.). It is not known, however, if the α1-ACT mRNA or protein(s) synthesized in brain are structurally equivalent to or distinct from one or more of the forms of α1-ACT synthesized by the liver and present in the plasma.

The diagnosis of Alzheimer's disease requires a detailed clinical evaluation, and diagnosis generally cannot be made until significant symptoms of dementia and memory loss are clinically apparent. Unfortunately, no practicable in vitro biochemical diagnostic test is presently available for diagnosing AD in its early stages and for identifying AD candidates. Koo et al. (1991) op.cit. report data indicating that increased expression of RNA that hybridizes to α1-ACT DNA probes in the brain increases with age and is associated with astrocytosis. Expression of mRNA that hybridizes to α1-ACT DNA probes is apparently associated with astrocytosis and/or astrogliosis, which characterize many different neuropathological conditions (e.g., Alzheimer's disease and certain CNS neoplasms). Matsubara et al. (1990) op.cit. were unable to demonstrate that measurement of α1-ACT in serum is a sufficiently selective and sensitive method for identifying AD patients, and alternatively have suggested that while measuring serum levels of α1-ACT may eventually be useful as a biochemical diagnostic marker of AD, there is presently no useful biochemical marker available. Moreover, even the equivocal results of Matsubara et al. have not yet proven to be reproducible.

Therefore, since α1-ACT mRNA levels in brain tissue are increased in AD and other neurodegenerative disorders, there exists a need in the art for methods and compositions for identifying and quantitating α1-ACT species that are produced in brain tissue and for distinguishing the brain α1-ACT signal from the background liver-produced α1-ACT present in the serum. These methods and compositions could be applied to develop diagnostic methods and kits for detecting the presence of or predisposition to a neurological disease, such as a neurodegenerative disease (e.g., Alzheimer's disease), or for use as cell type-specific markers for cells derived from the central nervous system (e.g., astroglial cells), such as in metastatic brain tumors.

SUMMARY OF THE INVENTION

Figure 1A:
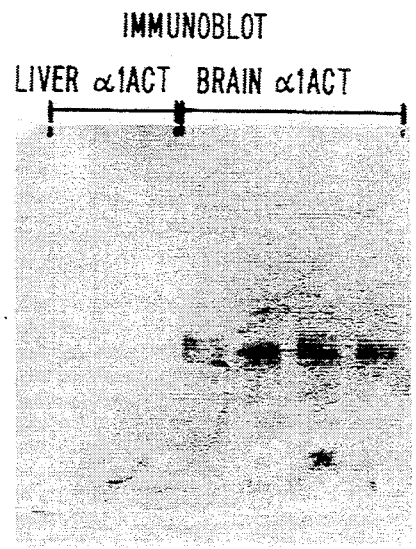
FIG. 1(a) is an immunoblot comparing the liver reactivity of the lectin *Aleuria aurantia* agglutinin for liver α1-ACT and brain α1-ACT.

It is an object of the invention to provide methods for identifying and substantially purifying a human brain α1-ACT, generally by the steps of: (1) generating a protein extract of human brain tissue, (2) purifying an α1-ACT fraction from the brain extract, (3) detecting, in the purified α1-ACT fraction, a structural feature (e.g., an N-linked glycan) that is present in the α1-ACT fraction from the brain extract but which is weakly detected or not detected in a α1-ACT fraction from human serum or human liver, and (4) isolating purified brain α1-ACT having said structural feature.

It is an object of the present invention to provide methods for detecting and quantifying a concentration of a brain-derived αl-antichymotrypsin species in biological samples, such as a sample of a biological fluid or a tissue biopsy sample.

It is another object of the present invention to provide compositions containing specific binding components that specifically bind or preferentially bind to a brain α1-ACT but do not substantially bind α1-ACT produced by the liver.

It is a further object of the invention to provide methods for developing diagnostic methods and diagnostic kits for determining the concentration of a brain α1-ACT in a biological sample. These methods and kits will typically comprise a first binding component that specifically binds human α1-ACT isoforms, and a second binding component that specifically or preferentially binds a structural feature (e.g., an N-linked glycan) that is present in a brain α1-ACT but which is not present in liver α1-ACT at detectable levels. Generally, the second binding component in a binding reaction under suitable binding conditions will preferentially bind to complex N-linked glycan structures which are present in brain α1-ACT but which are not present in liver α1-ACT; the second binding component generally binds to brain α1-ACT with an affinity of at least about $1 \times 10^6 M^{-1}$. In general, the complex N-linked glycan structures that are recognized (i.e., specifically bound) by the second binding component are carbohydrate epitopes of brain α1-ACT that bind to *Aleuria aurantia* agglutinin.

The present invention also provides a method for diagnosing neuropathological conditions in a human patient, such as Alzheimer's disease, wherein a diagnostic assay (e.g., a sandwich immunoassay employing an antibody that binds α1-ACT species and a lectin that binds a brain α1-ACT N-linked glycan structure that is not detectable in liver α1-ACT) is used to determine if a predetermined pathognomonic concentration of brain α1-ACT is present in a biological sample from a human patient; if the assay indicates the presence of brain α1-ACT at or above such predetermined pathognomonic concentration, the patient is diagnosed as an Alzheimer's candidate. Modifications of the method are provided which adapt the diagnostic assay for use in the diagnosis of human neuropathological conditions other than Alzheimer's disease (e.g., other neurodegenerative diseases producing enhanced levels of brain α1-ACT).

DEFINITIONS

For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference).

As used herein, "isoform" refers to one of at least two distinct polypeptide species that are essentially encoded by the same gene. An isoform is distinguished as having a unique primary amino acid sequence, a unique glycosylation pattern (i.e., glycoform), or a unique combination of primary amino acid sequence and glycosylation pattern. Multiple isoforms of a protein, such as APP or α1-ACT proteins, can be produced from a single gene by a variety of mechanisms, including alternative RNA splicing, post-translational proteolytic processing, cell type-specific glycosylation(s), and other mechanisms. For example, the noted amino-terminal microheterogeneity of α1-ACT (see, Background, supra) indicates that there are at least two, and likely at least three, isoforms of liver α1-ACT. Moreover, the identification of at least three microheterogeneous glycan structures in α1-ACT from serum implies the existence of several isoforms of α1-ACT in serum, differing in primary sequence and/or glycan structure(s). The mechanisms responsible for generating the various α1-ACT isoforms have not been defined precisely.

"Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. The specific site of attachment is typically signaled by a sequence of amino acids, referred to herein as a "glycosylation site sequence". The glycosylation site sequence for N-linked glycosylation is: -Asn-X-Ser- or -Asn-X-Thr-, where X may be any of the conventional amino acids, other than proline. The predominant glycosylation site sequence for O-linked glycosylation is: (Thr/Ser)-Xaa-Xaa-Pro-(SEQ. ID. NO:2)), where Xaa is any conventional amino acid. The recognition sequence for glycosaminoglycans (a specific type of sulfated sugar) is -Ser-Gly-Xaa-Gly-(SEQ. ID. NO:3), where Xaa is any conventional amino acid. The terms "N-linked" and "O-linked" refer to the chemical group that serves as the attachment site between the sugar molecule and the amino acid residue. N-linked sugars are attached through an amino group; O-linked sugars are attached through a hydroxyl group. However, not all glycosylation site sequences in a protein are necessarily glycosylated; some proteins are secreted in both glycosylated and nonglycosylated forms, while others are fully glysosylated at one glycosylation site sequence but contain another glycosylation site sequence that is not glycosylated. Therefore, not all glycosylation site sequences that are present in a polypeptide are necessarily glycosylation sites where sugar residues are actually attached. The initial N-glycosylation during biosynthesis inserts the "core carbohydrate" or "core oligosaccharide" (*Proteins, Structures and Molecular Principles*, (1984) Creighton (ed.), W. H. Freeman and Company, New York, which is incorporated herein by reference). Laine et al. (1991) op.cit. asserts that there are four potential glycosylation sites in α1-ACT from serum which corresponds to the number of sites given by Chandra et al. (1983) op.cit. However, Rubin et al. (1990) op.cit. indicates that there are six potential glycosylation sites in α1-ACT.

As used herein, "glycosylating cell" is a cell capable of glycosylating proteins, particularly eukaryotic cells capable of adding an N-linked "core oligosaccharide" containing at least one mannose residue and/or capable of adding an O-linked sugar, to at least one glycosylation site sequence in at least one polypeptide expressed in said cell, particularly a secreted protein. Thus, a glycosylating cell contains at least one enzymatic activity that catalyzes the attachment of a sugar residue to a glycosylating site sequence in a protein or polypeptide, and the cell actually glycosylates at least one expressed polypeptide. For example but not for limitation, mammalian cells are typically glycosylating cells. Other eukaryotic cells, such as insect cells and yeast, may be glycosylating cells. It is recognized that different cell types have different relative abundances of the various glycosylating enzymes, producing, in some cases, cell type-specific glycosylation patterns. With respect to α1-ACT, both brain cells (e.g., astrocytes) and liver cells (e.g., hepatocytes) are glycosylating cells, although cell-type specific glycosylation patterns can be present.

The terms "substantial similarity" or "substantial homology" as used herein denotes a characteristic of a polypeptide sequence or nucleic acid sequence, wherein the polypeptide sequence has at least 50 percent sequence identity compared to a reference sequence, and the nucleic acid sequence has at least 70 percent sequence identity compared to a reference sequence. The percentage of sequence identity is calculated excluding small deletions or additions which total less than 25 percent of the reference sequence. The reference sequence may be a subset of a larger sequence, such as a α1-antichymotrypsin sequence; however, the reference sequence is at least 18 nucleotides long in the case of polynucleotides, and at least 6 amino acid residues long in the case of a polypeptide.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g. $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein, the term "enriched" refers to composition or fraction wherein an object species has been partially purified such that, on a molar ratio basis, at least about 10 percent of one or more naturally occurring contaminant species have been removed. For example, a serum sample from an AD patient may be enriched for brain α1-ACT by selectively isolating macromolecular species that bind to AAA lectin; thus, a serum sample from an AD patient may chromatographed over a AAA lectin column, and the eluted retained fraction(s) are thereby enriched for brain α1-ACT.

As used herein "normal blood" or "normal human blood" refers to blood from a healthy human individual who does not have active Alzheimer's disease or other neuropathological disorder, or an identified predisposition for developing a neuropathological disease. Similarly, "normal serum", "normal plasma", "normal urine", and "normal CSF" refer to the respective fluids obtained from a healthy human individual who does not have active Alzheimer's disease or other neuropathological disorder.

As used herein "pathognomonic concentration" refers to a concentration of an analyte in a sample, for example the concentration of brain α1-ACT in a blood, plasma, serum, urine, or CSF sample, that indicates the presence of a specific disease or a predisposition to developing a specific disease, such as Alzheimer's disease. A pathognomonic concentration is a concentration of an analyte that falls outside the range of normal clinical values that is established by prospective and/or retrospective statistical clinical studies. Generally, an individual having a neurodegenerative disease (e.g., Alzheimer's disease) will exhibit a concentration of brain α1-ACT in a tissue or biological fluid sample that is higher than the range of concentrations that characterize normal, undiseased individuals; typically the pathognomonic concentration is at least about one standard deviation above the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

DETAILED DESCRIPTION

In accordance with the present invention, the concentration(s) of brain α1-ACT in biological tissue and fluid samples is measured. Detection of a pathognomonic concentration of α1-ACT in a sample taken from an individual generally indicates that the individual has an active neuropathological condition or is predisposed to developing a clinically apparent neuropathological condition in the future. A positive result (i.e., detection of a pathognomonic concentration of a brain α1-ACT in the sample) is considered as a diagnostic factor in a clinical differential diagnosis of disease. Neuropathological conditions may include, but are not limited to, the following examples: (1) neurodegenerative diseases, such as Alzheimer's disease, Parkinson's disease, and Huntington's disease, (2) CNS neoplasms, such as gliomas, astrocytomas, and malignant tumors of glial cell origin, and (3) inflammatory diseases, such as CNS inflammatory diseases, including, but not limited to: multiple sclerosis, acute disseminated encephalitis, viral encephalitis, bacterial encephalitis, and others.

Brain α1-ACT

As discussed supra, in humans there are several isoforms of α1-ACT encoded by the single copy α1-ACT gene on human chromosome 14. The basis of the present invention is the surprising discovery of a distinct α1-ACT isoform that can be detected in tissue samples or fluid extracts from the human brain, but which is relatively nonabundant in normal human blood. This type of isoform, which is present in the brain but which is rare or absent in normal human blood, is referred to as brain α1-ACT. Brain α1-ACT is a brain glycoprotein that has substantial homology to liver α1-ACT isoforms (i.e., amino acid sequences having substantial homology) and which specifically binds to *Aleuria aurantia* agglutinin. Brain α1-ACT is characterized, at least in part, by the property of preferentially binding to the lectin *Aleuria aurantia* agglutinin ("AAA lectin") with an affinity that is at least about 10 times greater than is the binding affinity of AAA lectin for α1-ACT present in normal serum, preferably with an affinity that is at least about 50 times greater, and more preferably with an affinity that is at least about 100 to 1000 times greater or more. Thus, brain α1-ACT comprises at least one isoform that specifically binds to AAA lectin. The discovery of brain α1-ACT and of specific binding components that preferentially recognize brain α1-ACT is the basis for diagnostic methods that are used to identify and measure brain α1-ACT in biological samples (e.g., a blood, plasma, serum, urine, or CSF fluid sample or CNS tissue biopsy sample).

AAA Lectin

The lectin *Aleuria aurantia* agglutinin is a protein composed of two identical subunits having no carbohydrate chain and possessing selective affinity for various glycoconjugates that contain L-fucose in their carbohydrate chain (Fukumori et al. (1990) *J. Biochem.* 107: 190, which is incorporated herein by reference). Methods for purifying AAA lectin have been reported as has expression of AAA lectin from a cDNA clone encoding it in *E. coli* (Nagata et al. (1991) *Biochim. Biophys. Acta* 1076: 187; Debray and Montreuil (1989) *Carbohydr. Res.* 185: 15; Fukumori et al. (1989) *FEBS Letters* 250: 153; EP 0 387 861, which are incorporated herein by reference). In general, the AAA lectin presents the highest affinity towards α(1→6)-linked L-fucosyl groups, and the presence of α(1→3)-linked L-fucosyl groups enhances the affinity of AAA lectin for α(1→6)-linked L-fucosyl groups; thus, the AAA lectin is suitable for resolving L-fucosylated glycopeptides (Debray and Montreuil (1989) op.cit.; Yamashita et al. (1985) *J. Biol. Chem.* 260: 4688). Thus, the AAA lectin is generally specific to α(1→6) L-fucosyl residues on complex N-linked glycan structures, and also recognizes α(1→3)-linked L-fucosyl groups.

The AAA lectin has significantly greater reactivity (i.e., binding affinity) with purified α1-ACT from brain tissue versus purified α1-ACT from plasma. This surprising result identifies carbohydrate differences between the purified α1-ACT from brain and plasma. Brain α1-ACT that is released into CSF or plasma can be identified (when present) and distinguished from α1-ACT isoforms that are not produced in the brain (e.g., liver-derived α1-ACT) on the basis of these observed structural differences.

Diagnostic and Therapeutic Applications

A change (typically an increase) in the level of brain α1-ACT in a biological sample from an individual which is outside the range of clinically established normal levels indicates the presence of an active neuropathological disease or condition in the individual from whom the sample was obtained and/or indicates a predisposition of the individual for developing (or progressing through) the disease. Typically, the neuropathological disease or condition thus diagnosed is a neurodegenerative disease, such as Alzheimer's disease. Thus, detection of a pathognomonic concentration of brain α1-ACT in a patient sample, such as a blood, plasma, serum, or CSF sample, is an indicator of Alzheimer's disease.

Further, brain α1-ACT may be used as a differentiation marker to identify and type cells of certain lineages and developmental origins. For example, detection of brain α1-ACT may be used to type a cell as being of mesodermal origin, as being a cell typically found in the CNS, and/or as being a CNS glial cell (e.g., an astrocyte). Such cell-type specific detection may be used for histopathological diagnosis of neoplasms (e.g., for diagnosing the cell type and/or differentiation state of a primary brain tumor cell) or other applications (e.g., localizing imaging or toxic agents to specific locations in the brain for magnetic imaging or radioimaging in vivo or for cytotoxic effect). Such agents may include, for example, a linked component comprising: metals, chemotherapeutic drugs, radiosensitizing agents, cellular toxins, radionuclides, and others.

Various other applications of such agents that specifically detect brain α1-ACT are apparent to those of skill in the art and may be developed. For in vivo applications involving agents that specifically bind α1-ACT, it is desirable that the agents are either directly injected into the brain or CSF, or are able to cross the blood-brain barrier. Examples of derivatived proteins (such as antibodies) and peptidomimetics capable of facile transfer across the blood-brain barrier are known to those of skill in the art, and equivalent agents for binding to α1-ACT may be readily developed using methods available in the art. Frequently, it will be desirable or necessary to introduce the pharmaceutical compositions directly or indirectly into the brain. Direct techniques usually involve placement of a drug delivery catheter into the host's brain ventricular system to bypass the blood-brain barrier. Indirect techniques, which are generally preferred, involve formulating compositions to provide for drug latentiation by the conversion of hydrophilic drugs into lipid-soluble drugs. Latentiation is generally achieved through blocking the hydroxyl, carboxyl, and primary amine groups present on the drugs to render the drug more lipid soluble and amenable to transportation across the blood-brain barrier. Alternatively, the delivery of hydrophilic drugs can be enhanced by intra-arterial infusion of hypertonic solutions which can transiently open the blood-brain barrier.

Detection of Brain α1-ACT in Samples

The identification and measurement of brain α1-ACT in a biological sample can be performed by one or more assay methods of the invention. The general scheme of such an assay method requires that a biological sample is obtained from a human patient. The biological sample is typically a fluid, such as CSF, urine, saliva, blood, or a blood fraction (e.g., plasma or serum), although tissue biopsy material, such as a brain biopsy sample, may be used. When a tissue sample is used, it is generally preferred that an extract of the tissue sample is made (e.g., by homogenizing the tissue in a suitable extraction buffer) and, if desired, partially purified by one or more procedures (e.g., affinity chromatography, ion exchange chromatography, HPLC, centrifugation, and others) so that a fraction containing brain α1-ACT, if present in the original sample, is thus produced. Whether a tissue extract is made or a biological fluid sample is used, it is often desirable to dilute the sample in one or more diluents that do not substantially interfere with subsequent assay procedures. Generally, suitable diluents are aqueous solutions containing a buffer system (e.g., 50 mM NaHPO$_4$ or 5–100 mM Tris, pH4–pH10), non-interfering ionic species (5–500 mM KCl or NaCl, or sucrose), and optionally a nonionic detergent such as Tween. The sample, either straight or diluted, is then analyzed for the diagnostic analyte, brain α1-ACT, by one of the following generally applicable methods.

Specific Binding Assays

Brain α1-ACT which is released into a biological fluid or which is present in an extract of a tissue sample (e.g., homogenized brain biopsy) can be detected and discriminated from plasma α1-ACT isoforms by a specific binding assay.

Specific binding assays are commonly divided into homogeneous and heterogeneous assays. In a homogeneous assay, the signal emitted by the bound labeled component is different from the signal emitted by the unbound labeled component, hence the two can be distinguished without the need for a physical separation step. In heterogeneous assays, the signal emitted from the bound and unbound labeled components is identical, hence the two must be physically separated in order to distinguish between them. The classical heterogeneous specific binding assay is the radioimmunoassay (RIA) (Yalow et al. (1978) *Science* 200: 1245, which is incorporated herein by reference). Other heterogeneous binding assays include the radioreceptor assay (Cuatrecasas et al. (1974) *Ann. Rev. Biochem.* 43: 109), the sandwich radioimmunoassay (U.S. Pat. No. 4,376,110, which is incorporated herein by reference), and the antibody-/lectin sandwich assay (EP 0 166 623, which is incorporated herein by reference). Heterogeneous assays are usually preferred, and are generally more sensitive and reliable than homogeneous assays.

In the general method of the invention, brain $\alpha$1-ACT in a sample is detected and quantified by contacting a sample with a binding component that specifically or preferentially binds to brain $\alpha$1-ACT to form a bound complex, and then detecting the formation of bound complex, typically by measuring the presence of label in a labeled binding component present in the bound complexes.

In the present method of the invention, brain $\alpha$1-ACT in a sample is detected and measured by: (1) contacting the sample with an $\alpha$1-ACT binding component, typically an antibody or antibody fragment, that specifically binds $\alpha$1-ACT isoforms, including brain $\alpha$1-ACT, and (2) contacting the sample with a carbohydrate binding component, typically a lectin, that binds to N-linked glycan structures that are present on brain $\alpha$1-ACT but are substantially absent in $\alpha$1-ACT isoforms present in normal blood, and (3) measuring the formation of bound complexes formed between the sample and the $\alpha$1-ACT binding component and carbohydrate binding component. Typically, brain $\alpha$1-ACT in the sample forms a complex with the $\alpha$1-ACT binding component and the carbohydrate binding component essentially simultaneously, forming a complex comprising brain $\alpha$1-ACT and the two binding components. However, the invention can be practiced by contacting the sample (or partially purified fraction thereof) sequentially with the $\alpha$1-ACT binding component and the carbohydrate binding component (in either order of presentation) and measuring the formation of a complex between brain $\alpha$1-ACT and a binding component. In certain embodiments the brain $\alpha$1-ACT detected by the binding assay is a brain glycoform of $\alpha$1-ACT.

An $\alpha$1-ACT binding component specifically binds $\alpha$1-ACT isoforms. Thus, an $\alpha$1-ACT binding component generally has a binding affinity that is at least about 10- to 100-fold higher (as measured by the dissociation constant, $K_D$, which decreases as binding affinity increases, so that a $K_D$ of $1 \times 10^{-1}$M indicates a lower affinity that a $K_D$ of $1 \times 10^{-9}$M) for $\alpha$1-ACT isoforms than for other naturally-occurring proteins in the blood, serum, or plasma of a human. For example, an antibody that is an $\alpha$1-ACT binding component typically has the property of identifying a single band (which may be comprised of several $\alpha$1-ACT isoforms) on an immunoblot (e.g., a Western blot) of a denaturing polyacrylamide electrophoresis gel loaded with human blood proteins. Such antibodies are generally referred to as being monospecific for $\alpha$1-ACT isoforms.

A carbohydrate binding component preferentially binds to N-linked glycan structures that can be specifically bound to *Aleuria aurantia* agglutinin. Such N-linked glycan structures are generally characterized by the presence of at least one $\alpha(1 \rightarrow 6)$-fucose moiety and-/or a $\alpha(1 \rightarrow 3)$-fucose moiety, but preferably at least one $\alpha(1 \rightarrow 6)$-fucose moiety. Specifically, a carbohydrate binding component of the invention specifically binds to at least one carbohydrate moiety that is present on brain $\alpha$1-ACT but which is substantially absent on liver $\alpha$1-ACT. Thus, AAA-lectin is one example of a carbohydrate binding component of the invention, although other carbohydrate binding components, such as antibodies (e.g., anti-fucosyl antibodies, anti $\alpha(1 \rightarrow 6)$fucose antibodies), could be used. Assays of the invention are generally performed using a predetermined amount of a carbohydrate binding component that preferentially binds to complex N-linked glycan structures that bind to *Aleuria aurantia* agglutinin with an affinity of typically at least about $1 \times 10^6 M^{-1}$, preferably with an affinity of at least about $1 \times 10^7 M^{-1}$, to $1 \times 10^8 M^{-1}$, more preferably with an affinity of at least about $1 \times 10^9 M^{-1}$ or more.

In one embodiment, the $\alpha$1-ACT binding component binds to $\alpha$1-ACT isoforms, including brain $\alpha$1-ACT, preferably by binding to one or more shared epitopes which are common to several $\alpha$1-ACT isoforms (e.g., a peptide epitope). Binding with the first binding component is performed to select $\alpha$1-ACT isoforms from the sample (e.g., by affinity chromatography or other reversible binding step) to produce a purified $\alpha$1-ACT fraction. The purified $\alpha$1-ACT fraction is then reacted with the carbohydrate binding component which binds preferentially or specifically to a carbohydrate moiety that is present on brain $\alpha$1-ACT but is substantially absent on $\alpha$1-ACT isoforms that are detectable in normal blood (whole blood, plasma, serum, or other purified or enriched blood fraction). Alternatively, the order of contacting may be reversed so that, for example, a sample is contacted with AAA lectin to select bound species having carbohydrate structures similar to that of brain $\alpha$1-ACT and the lectin-bound glycoproteins eluted and then reacted with one or more antibodies that specifically bind to $\alpha$1-ACT isoforms to yield a detectable complex. Thus, in some embodiments the carbohydrate binding component (e.g., AAA lectin) is immobilized on a solid substrate and the $\alpha$1-ACT binding component is soluble unless immobilized by binding to a brain $\alpha$1-ACT that is bound to the carbohydrate binding component; in variations of these embodiments, the $\alpha$1-ACT binding component is labeled directly (e.g., by covalent attachment of label or by radioisotopic incorporation) or by reaction with a labeling component that binds specifically to the $\alpha$1-ACT binding component (e.g., a labeled second antibody).

Binding assays of the invention are typically carried out in reaction vessels under suitable binding conditions, which may be selected by those of skill in the art. Various examples of suitable binding conditions useful in these assays are discussed, for example, in Harlow and Lane, *Antibodies: A Laboratory Manual*, Cold Spring Harbor, N.Y. (1988), which is incorporated herein by reference. In general, suitable binding conditions include an aqueous binding buffer containing a salt (e.g., 5–500 mM NaCl or KCl), a buffer (e.g., TRIS or phosphate buffer at pH 4–10), and optionally a nonionic detergent (e.g., Tween). In some embodiments, proteinase inhibitors or stabilizers may be included. The binding reactions are conducted for a suitable binding period, which is typically at least about 1 to 5 minutes, preferably at least about 30 minutes to several hours, although typically less than about 24 hours, more preferably less than about a few hours or less. Binding reactions (including washes) are typically carried out a temperature range of about 0° C. to about 45° C., preferably about 4° C. to about 20°-25° C.

Preferred Embodiment

Although many variations of the invention are possible, including assays using a single antibody that is essentially monospecific for brain α1-ACT and competitive immunoassays, a two-component sandwich binding assay is believed to be generally preferable. In one embodiment of a sandwich binding assay, an immobilized binding component binds to a site on brain α1-ACT and a soluble labeled binding component binds to a second site on the brain α1-ACT, unbound components are removed (typically by washing with a suitable buffered solution and/or centrifugation), and the amount of labeled binding component that remains immobilized via linkage through the analyte (i.e., brain α1-ACT) is quantitatively measured to determine the amount of brain α1-ACT present in the sample. Some sandwich assays require addition of immobilized binding component and analyte (i.e., sample) followed by separation of bound and unbound analyte, then followed by addition of soluble labeled binding component. Although it is possible to practice the invention in alternative ways, it is believed that in most instances at present it is preferable that the immobilized binding component is an α1-ACT binding component (either monoclonal antibody(ies) or a polyclonal antiserum) that selectively binds α1-ACT isoforms, including brain α1-ACT, and that the soluble labeled binding component (the carbohydrate binding component) be subsequently added. Since antibodies generally have superior binding affinity and specificity, it is desirable that both the α1-ACT binding component and the carbohydrate binding component are antibodies, although typically the carbohydrate binding component will be a lectin, such as AAA lectin.

Where the α1-ACT binding component is an antibody, the antibody typically binds to α1-ACT isoforms with a binding affinity for brain α1-antichymotrypsin of at least about $1 \times 10^7 M^{-1}$, preferably with an affinity of at least about $1 \times 10^8 M^{-1}$, and more preferably with an affinity of at least about $1 \times 10^9 M^{-1}$ to $1 \times 10^{11} M^{-1}$ or more. Polyclonal antiserum can be affinity purified by chromatography over a α1-ACT-Sepharose column (made by linking purified α1-ACT to a CNBr-activated Sepharose column), typically generating a purified antiserum with higher affinity and/or binding specificity.

Antibodies that are used as α1-ACT binding components should be non-interfering antibodies. A noninterfering antibody binds to α1-ACT isoforms but does not significantly interfere with the binding of a carbohydrate binding component to a brain α1-ACT. Thus, an antibody that binds to a carbohydrate moiety which is shared among (i.e., common to) α1-ACT isoforms (e.g., a core carbohydrate) should not substantially interfere (e.g., by steric hindrance) with binding of AAA lectin to a brain α1-ACT so that the brain α1ACT cannot be detected by a labeled AAA lectin.

Although the invention can be practiced with α1-ACT-specific monoclonal antibodies or polyclonal antisera serving as an α1-ACT binding component, antibodies other than 7D7 and 16D2 can be produced and used provided that they recognize and preferentially bind to brain α1-ACT. Using the methods disclosed herein, others skilled in the art can readily produce equivalent reagents. Moreover, methods (Kohler and Milstein (1976) *Eur. J. Immunol.* 6: 511, incorporated herein by reference) are known for producing a monoclonal antibody, such as one that binds to a brain α1-antichymotrypsin with an affinity of typically at least about $1 \times 10^6 M^{-1}$, preferably at least about $1 \times 10^8 M^{-1}$ and more preferably at least about $1 \times 10^9$ to $1 \times 10^{11} M^{-1}$ or more, and which has a binding affinity for a liver α1-antichymotrypsin of at least about 10-fold less, preferably at least about 100- to 1000-fold less, with a sufficient difference in binding affinity between brain α1-ACT and liver α1-ACT so as to be a specific binding component (i.e., to detect the presence of brain α1-ACT by discrimination from liver α1-ACT). In general terms, such a method comprises the steps of: (1) immunizing an animal with a composition containing an immunogenic dose of brain α1-antichymotrypsin (or a fragment thereof), usually at least about 50 to 500 μg of purified material, typically co-administered with an adjuvant, (2) harvesting B-cells from the animal, (3) fusing the B-cells with a myeloma to generate a bank of hybridoma clones, and (4) selecting, from the bank, a hybridoma clone that expresses a monoclonal antibody which binds to a brain α1-antichymotrypsin with an affinity of at least about $1 \times 10^7 M^{-1}$ and which has a binding affinity for a liver α1-antichymotrypsin of at least about 10- to 1000-fold lower.

Additionally, a method for producing a polyclonal antiserum that specifically or preferentially binds to a brain α1-antichymotrypsin is described. In general, such a polyclonal antiserum will have an affinity for brain α1-ACT of at least $1 \times 10^8 M^{-1}$ and which has a binding affinity for liver α1-antichymotrypsin of at least about 10- to 1000-fold lower, comprising the steps of: (1) immunizing an animal with a composition containing an immunogenic dose of a brain α1-antichymotrypsin or a fragment thereof (and typically an adjuvant), (2) obtaining a polyclonal antiserum from said animal, (3) preadsorbing said polyclonal antiserum with a saturating amount of a liver α1-antichymotrypsin, and (4) recovering antibodies that do not substantially bind to the liver α1-antichymotrypsin.

α1-ACT binding components which contain carbohydrate moieties, such as L-fucosyl moieties (e.g., α(1→6)-fucose) can potentially interfere with the binding assay by binding to a carbohydrate binding component in the absence of brain α1-ACT, producing a false signal. Thus, it is preferred that α1-ACT binding components do not contain interfering carbohydrate moieties. Many naturally-occurring antibodies are composed of glycosylated immunoglobulin chains, and are preferably chemically oxidized (e.g., with sodium periodate) to oxidize the carbohydrate(s) prior to use as an α1-ACT binding component. Alternatively, immunoglobulins may be produced in a non-glycosylating cell (or other synthesis system), or may be produced in a glycosylating cell but may have one or more glycosylation sites removed by site-directed mutagenesis of an encoding nucleotide sequence to ablate a glycosylation site sequence.

Immobilized binding components (which may be either the α1-ACT binding component or the carbohydrate binding component) can be produced by precoating the reaction vessel (e.g., a microtiter well or polymer membrane) to form non-covalent linkages, or to form covalent linkages, for example by chemical cross-linking. Alternatively, the solid phase can be produced during or subsequent to incubation of the assay mixture containing the sample and a first binding component, permitting both the first binding component and the analyte to be soluble during the reaction incubation.

Since reactants equilibrate more rapidly when all reactants are in solution, such an approach offers shorter incubation times than traditional methods using preformed insoluble binding components. In either case, the analyte eventually is bound to an immobilized binding component and soluble labeled binding component is allowed to bind to the analyte for a predetermined period (i.e., developed for standardization and optimization at the discretion of the practitioner), followed by removal of the unbound labeled binding component, usually by washing the immobilized phase with wash buffer for at least one washing period (generally from about 2 seconds to about 24 hours). The remaining immobilized labeled binding component is a measure of the brain α1-ACT that was present in the sample and can be calculated precisely by generation of a standard curve.

Detection of bound "sandwich" complexes typically is performed by detecting the presence of bound labeled binding component. Usually, the labeled binding component comprises a direct label, such as a fluorescent label, radioactive label, or enzyme-conjugated label that catalyzes the conversion of a chromogenic substrate to a chromophore. However, it is possible, and often desirable for signal amplification, for the labeled binding component to be detected by at least one additional binding component that incorporates a label. Signal amplification can be accomplished by layering of reactants where the reactants are polyvalent. Direct labeling of binding components may be accomplished by various methods known in the art, including: covalent attachment of various enzymes (e.g., horseradish peroxidase, β-galactosidase, and alkaline phosphatase), fluorescent molecules (fluorescein isothiocyanate, rhodamine, dansyl chloride), and radioactive materials ($^3$H, $^{14}$C, $^{32}$P, $^{35}$S, $^{125}$I, $^{131}$I) which may be incorporated as labeled amino acid residues or post-translationally labeled (e.g., Chloramine T method).

Diagnostic Kits

The invention also encompasses diagnostic kits that typically contain the assay reagents in a prepackaged form. The assay components will typically include α1-ACT binding component, carbohydrate binding component, labeled component (which may be attached or incorporated into the α1-ACT binding component or the carbohydrate binding component, or may be provided separately), a suitable reaction vessel (e.g., a microtiter well, a polymer membrane), and may also include diluent(s), assay buffer(s), wash buffer(s), and development reagents (e.g., chromogenic substrate for enzyme-linked assays). The various assay components are usually provided in aqueous solution, but may be provided in lyophilized form and reconstituted for performing the assay. Similarly, automated devices may be developed to perform assays of the invention.

EXPERIMENTAL EXAMPLES

Purification of α1-Antichymotrypsin

Human plasma or brain tissue from normal and Alzheimer's disease (AD) patients were used for the purification of α1-ACT. Brain tissue was homogenized on ice with an Omni mixer in homogenization buffer containing 20.0 mM TRIS-HCl, pH 7.5, 5.0 mM EDTA, 150 mM NaCl, 1% betaoctylglucoside, 10 micrograms per milliliter (ug/ml) leupeptin, 1.0 mM phenylmethylsulfonylfluoride (PMSF), 0.1 mM 4-(2-aminoethyl)-benzenesulfonylfluoride HCl (AEBSF) at 0° C. As a general rule, 5 milliliters (ml) of homogenization buffer was used per gram of wet tissue. The following purification steps were used in purifying either the brain or plasma form of α1-ACT. While stirring on ice, polyethylene glycol (PEG) 8000 at 50% (w/v) was added to the brain homogenate or plasma to a final concentration of 10% PEG and kept stirring for 30 minutes on ice. The material was centrifuged in a Beckman J2-21M centrifuge (Beckman Instruments, Fullerton, Calif.) using a JA10 rotor at 8,500 rpm for 30 minutes at 4° C. The supernatant was decanted into a glass container and the pellet is discarded. PEG at 50% was slowly added to the supernatant while stirring on ice to a final concentration of 25% PEG. As described in the first PEG step, the material was stirred on ice for 30 minutes and centrifuged. After the second PEG precipitation, the supernatant was discarded and the pellet was resuspended in 30 mM NaHPO$_4$, pH 7.0 and 50 mM NaCl.

All of the following purification steps were performed at 4° C. The resuspended pellet material was run over a DEAE-Sepharose column (Pharmacia LKB, Piscataway, N.J.) that had been equilibrated in 20 mM NaHPO$_4$, pH 7.0 and 50 mM NaCl. The bound material was eluted with a linear gradient of 50 mM NaCl to 350 mM NaCl in 20 mM NaHPO$_4$, pH 7.0 buffer. An immunoassay for α1-ACT was used to screen the fractions eluted from each of the column runs and is described in Experimental Procedures following the purification procedures. The positive immunoreactive fractions were pooled and dialyzed to 20 mM Tris-HCl, pH 8.0 at 4° C. using Spectra/Por dialysis tubing (Spectrum, Houston, Tex.) with a molecular weight cut-off of 12,000–14,000 M$_r$ with at least two buffer changes as were all subsequent dialysis steps throughout the purification. The dialyzed material was run over a 50–100 mesh Affi-Gel Blue column (BioRad, Richmond, Calif.) equilibrated with 20 mM TRIS-HCl pH 8.0. The material was eluted using a linear gradient of 0–0.50M NaCl in 20 mM TRIS-HCl, pH 8.0. The positive immunoreactive fractions were pooled and dialyzed to 10 mM NaHPO$_4$, pH 7.0, and chromatographed on a DNA-cellulose column (Sigma, St. Louis, Mo.) equilibrated in 10 mM NaHPO$_4$, pH 7.0. A linear gradient of 0–0.40M NaCl in 10 mM NaHPO$_4$, pH 7.0 was run and the fractions were assayed for α1-ACT. The positive immunoreactive fractions were pooled and dialyzed to phosphate buffered saline (PBS; 8.0 mM Na$_2$HPO$_4$, 1.5 mM KH$_2$PO$_4$, 137 mM NaCl, 2.7 mM KCL, pH 7.5). To evaluate the purified α1-antichymotrypsin, SDS-polyacrylamide gel electrophoresis was performed, followed by immunoblot analysis using lectins, α1-ACT monoclonal antibodies (mAbs), and Coomassie blue stain.

The purified α1-ACT was also evaluated by amino acid analysis using a 420A Derivatizer (Applied Biosystems, Foster City, Calif.) and amino terminal sequence analysis using a 377A Protein Sequencer (Applied Biosystems). The amino-terminal sequence of liver α1-ACT generally begins at amino acid 24 and/or 26 (numbering convention based on full-length deduced polypeptide sequence). The amino acid sequence data from a preparation of brain α1-ACT is as follows:

-His-Pro-Xaa-Ser-Pro-Leu-Asp-Glu-Glu-Asn-Leu-Thr-Gln-Glu-Asn(SEQ. ID. NO:4)), where Xaa is any of the conventional amino acids. The data is representative of the amino-terminal sequence data received from other brain α1-ACT preparations, and is consistent with the amino-terminal sequence data of liver α1-ACT (op.-cit).

Immunoaffinity Purification of α1-Antichymotrypsin

The PEG steps described in the previous purification method were applied for both the plasma and brain purification for α1-ACT. The pellet from the second PEG precipitation was resuspended in PBS and centrifuged in a Beckman GPR tabletop centrifuge (Beckman Instruments, Fullerton, Calif.) at 2500 rpm for 15 minutes at 4° C. The matrix used for the immunoaffinity purification step was α1-ACT monoclonal antibodies (mAbs), 7D7 and 16D2, coupled to Affi-Gel Hz (BioRad, Richmond, Calif.) varying from 1-2.5 milligrams (mg) per 1 ml of matrix. The coupling procedure used was that of the manufacturer's for large-scale coupling. Fifty milliliters of supernatant which is equivalent to 25 ml of plasma or approximately 30 grams of wet brain tissue was incubated with 0.5 ml of 7D7-and 16D2-Affi-Gel Hz mix. The supernatant was incubated at 4° C. for at least 2 hours while gently mixing on a Nutator (Clay Adams, Parsippany, N.J). It was then spun in a tabletop centrifuge (Beckman GPR) at 2,000 rpm for 10 minutes at 4° C. The 7D7-and 16D2-Affi-Gel Hz matrix was washed four times with at least 5 ml of PBS using the same centrifugation step for separating the matrix from the starting material. The bound α1-ACT was eluted using 1.5 ml of 4.0M sodium isothiocyanate buffered in 10 mM TRIS-HCl, pH 7.5 for 0.5 ml of matrix. The eluted material was dialyzed to PBS at 4° C. with at least two buffer changes. The purified α1-ACT was analyzed by amino acid analysis, amino-terminal analysis, and SDS-polyacrylamide gel electrophoresis followed by immunoblot analysis using lectins and a polyclonal antibody to α1-ACT (Dako, Carpinteria, Calif.).

Immunoassay for α1-Antichymotrypsin

A competitive immunoassay format was used to quantitate α1-ACT by measuring fluorescence using a Screen Machine (IDEXX, Portland, Me.). The presence of α1-ACT in the samples being measured competes for the ability of FITC-α1-ACT to bind the α1-ACT antibody, and hence, reduces total fluorescence proportionately. The α1-ACT purified from plasma using the classic chromatography purification steps and analyzed by amino acid analysis and amino-terminal sequence analysis was used for standards in a range of 0.05-1.2 μg/ml. Twenty microliters (μl) per well of the α1-ACT standards and samples were added to a 96-well filter plate (IDEXX) followed by the addition of 20 μl per well of the FITC-labeled α1-ACT at 0.5 μg/ml. Then, the α1-ACT mAb 16D2 at 0.5 μg/ml was added to the wells by dispensing 20 μl per well. The samples and 16D2 were diluted into wash buffer which consists of PBS, 0.1% gelatin, 0.05% Tween-20 and 0.1% sodium azide ($NAN_3$). The mixture was incubated for 30 minutes at 21° C. At the end of the incubation period, 10 ul of goat anti-mouse IgG coupled to 0.8 micron polystyrene beads (IDEXX) were added per well of a 0.25% (w/v) solution in wash buffer followed by a 30 minute incubation at 21° C. The bead coupling protocol is discussed in the α1-ACT monoclonal antibody screening section of Experimental Procedures. After the incubation is complete, a programmed protocol for α1-ACT instructs the Screen Machine to separate, wash and read the plate. The first step of the program separates the beads by vacuum followed by four washes with wash buffer (without the gelatin) aspirated by vacuum and the level of fluorescence is automatically quantitated.

Production of α1-antichymotrypsin Monoclonal Antibodies

Monoclonal antibodies (mAbs) to α1-ACT were generated using Balb/c mice as the host following the methods of Kohler and Milstein (Kohler and Milstein (1976) *Eur. J. Immunol.* 6: 511, which is incorporated herein by reference), Each mouse was initially injected intraperitoneally with 50 μg of α1-ACT purified from human plasma in complete Freund's adjuvant, and subsequently injected with 50 μg of α1-ACT in Imject Alum (Pierce, Rockford, Ill.) every ten days with the final boost prior to the fusion in phosphate buffered saline (PBS). The mouse was fused four days after the final boost. The fusion protocol required the following materials: Dulbecco's Modified Eagle Media (DMEM) with high glucose (Gibco BRL, Grand Island, N.Y.); PEG 1500 (Boehringer Mannheim, Germany); fetal bovine serum (FBS; J. R. Scientific, Woodland, Calif.); 200 mM tissue culture grade L-glutamine (Gibco BRL); 10 mM tissue culture grade hypoxanthine (Sigma, St. Louis, Mo.); 200 μg/ml tissue culture grade azaserine (Sigma); 0.93% ammonium chloride (Sigma); 1.0M tissue culture grade HEPES buffer, pH 7.2 (Gibco BRL); one 35 mm sterile petri dish; sterile forceps; sterile dissecting scissors; twenty sterile 96-well flat bottom tissue culture plates with lids (Costar, Cambridge, Mass.); a twelve channel pipettor and sterile pipette tips; two sterile microscope slides with frosted ends; sterile 15 ml and 50 ml conical tubes; Sp2/0 cells from American Type Culture Collection (Rockville, Md.) grown to the specifications provided by the American Type Culture Collection.

Prior to the fusion two different mediums were prepared. The first is a growth medium containing 382.5 ml of DMEM, 100 ml of FBS, 5.0 ml of 200 mM L-glutamine, 7.5 ml of 1.0M HEPES buffer, pH 7.2, and 5.0 ml of 10 mM of hypoxanthine. The second medium, the selection media, comprises 44 ml of growth media, 50 ml spent Sp2/0 supernatant, 4.0 ml of FBS, 0.5 ml of 200 mL L-glutamine, 0.5 ml of 10 mM hypoxanthine and 1.0 ml of 200 μg/ml azaserine.

The mouse was sacrificed and then briefly immersed in 70% ethanol to sterilize. The mouse is then placed in a vertical flow hood where the spleen is aseptically removed. The spleen is immersed into 5.0 ml of growth media contained within a 35 mm petri dish, and it is dissociated between the frosted ends of the two slides. Once the clumps of residual connective tissue have settled, the supernatant should be a single cell suspension of spleen cells. The spleen cell suspension is placed into a sterile 15 ml tube followed by the addition of approximately 6.0 ml of growth media from three 2.0 ml washes of the petri dish and brought to a final volume of 15.0 ml with growth media. The cell suspension is spun in an IEC clinical centrifuge (International Equipment Co., Needham, Mass.) at $500 \times g$ (setting 4) for 10 minutes. After the centrifugation step is complete, the supernatant is removed from the cells, and they are resuspended in 7.0 ml of ammonium chloride at 4° C. This cell suspension is allowed to sit on ice for 5 minutes to allow the red blood cells in the spleen cell pellet to lyse.

In the meantime, the Sp2/0 cells were prepared for the fusion. The cells are generally greater than $5 \times 10^5$ cells per ml and less than $9 \times 10^5$ cells per ml with the viability of the cells being greater than 95% as determined by trypan blue exclusion. A 3:1 or 4:1 ratio of spleen cells:Sp2/0 cells is needed, and on average, $2 \times 10^8$ cells are obtained per spleen. Therefore, approximately $5 \times 10^7$ Sp2/0 cells are added to a sterile 50 ml conical tube and spun in a clinical centrifuge at $500 \times g$ for 10 minutes. The supernatant is saved for use in the selection media and the Sp2/0 cell pellet is resuspended in 15 ml of just DMEM.

When the incubation of the spleen cells was complete, the suspended spleen cells are removed from the debris pellet and added to the Sp2/0 cells, and DMEM is added to the spleen cell/Sp2/0 cell mixture to a final volume of 50 ml. The cells are centrifuged at 500×g for 10 minutes. The supernatant is removed from the pellet, and the pellet is loosened by vortexing. The actual fusion step takes place when 1 ml of PEG is added to the pellet while shaking and vortexing one time. The cells are incubated in the PEG solution for 1–2 minutes. Twenty-five ml of DMEM is added to the pellet and equilibrated for 1 minute, and then 25 ml of growth media is added and incubated for 1 minute. The cells are centrifuged for 10 minutes at 500×g and the supernatant is discarded and the pellet is resuspended in 100 ml of selection media. The cells are generally plated into twenty 96-well plates by adding 50 $\mu$l of the cell suspension per well using a 12-channel pipettor.

Two days following the fusion each well is fed 50 $\mu$l of growth media. On day five post fusion, 50 $\mu$l is removed and the fusion is fed 100 $\mu$l of growth media. Hybrids were visible between day seven and day ten post fusion, and it is at this time that the fusion was fed 100 $\mu$l of growth media. Screening generally begins on day ten post fusion.

$\alpha$1-Antichymotrypsin Monoclonal Antibody Screening Protocol

The hybrids were screened by a capture immunoassay format employing the Screen Machine (IDEXX, Portland, Me.) a fluorescent reader. When the hybrids are ready to screen, 20 ul of hybridoma tissue culture supernatant is drawn and added to a 96-well IDEXX filter plate. The supernatant is incubated with 20 ul per well of goat anti-mouse IgG coated onto 0.8 micron IDEXX polystyrene beads and incubated for 30 minutes at 21° C.

The beads for the capture assay are prepared by first washing 2.4 ml of 0.8 micron polystyrene beads (5% w/v) in coating buffer (100 mM NaHPO$_4$, pH 5.0). An Eppendorf 5415 centrifuge (Brinkmann, Westbury, N.Y.) is used to pellet the beads at 14,000 rpm for five minutes. The pellet is resuspended in a small amount of coating buffer, sonicated, and transferred to a 15 ml tube. This is followed by the addition of 2.4 mg of goat anti-mouse IgG (Jackson ImmunoResearch, West Grove, Pa.) to the beads. The mixture is brought to a final volume of 12 ml in coating buffer and incubated overnight at 21° C. while mixing on a Nutator. After adsorption, the beads are washed two times in wash buffer comprising of PBS, 0.1% gelatin and 0.1% NaN$_3$ and the beads are pelleted in a Beckman J2-21M centrifuge using a JA-17 rotor at 15,000 rpm for 15 minutes. The beads are resuspended in wash buffer to a final volume of 50 ml (0.2% w/v). These beads can be stored for 4–6 weeks at 4° C. without a detectable loss in activity.

After the hybridoma supernatant has been incubated with the goat anti-mouse IgG beads, the wells are aspirated by vacuum and washed one time with wash buffer. The Screen Machine then adds 20 ul per well of $\alpha$1-ACT-FITC at 5.0 ug/ml and incubated for 30 minutes. The mixture is automatically washed three times and the level of fluorescence quantitated. The positive hybrids are identified by the ability to "capture" fluorescent-labeled $\alpha$1-ACT and are rescreened by the same screening protocol. During this time, the positive hybrids are subcloned by the limiting dilution technique until they are stabilized. Positive hybrids, 7D7 and 16D2, were identified by the ability to capture (i.e., selectively bind to) $\alpha$1-ACT.

Ascites Production

Balb/c mice were injected with 0.5 ml of 2,6,10,14-tetramethylpentadecane (Pristane) intraperitoneally. Ten days later, the mice were injected with 2–5×10$^6$ hybridoma cells intraperitoneally, as well. Ascites should be evident by day ten post injection. The ascites is collected from the mice by draining with an 18 gauge needle into a sterile tube. A final concentration of 0.1% NaN$_3$ and 10 mM CaCl$_3$ is added to the tube of ascites. The hybridoma cells and red blood cells are removed by centrifugation at 1000×g for 10 minutes in an IEC clinical centrifuge. The ascites is allowed to clot overnight at 4° C., and then the clot is removed.

Antibody Purification

The ascites for 16D2 or 7D7 were diluted 1:1 with PBS. An equal volume of saturated NH4SO$_4$ is slowly added to the diluted ascites and is allowed to stir on ice for 30 minutes. The ascites is then spun in a Beckman J2-21M centrifuge at 15,000 rpm for 15 minutes at 4° C. The pellet is resuspended by adding PBS and saturated NH4SO$_4$ to their starting volumes and spun again, as described above. The pellet is resuspended in PBS and extensively dialyzed against 10 mM NaHPO$_4$, pH 8.0.

After dialysis, the partially purified antibody was chromatographed on a DEAE-Sepharose (Pharmacia LKB) column equilibrated with 10 mM NaHPO$_4$, pH 8.0. The bound material is eluted using a linear gradient of 0–0.5M NaCl in 10 mM NaHPO$_4$, pH 8.0. From the chromatograph, protein containing fractions are analyzed by 12% SDS-PAGE (sodium dodecyl sulfate-polyacrylamide gel electrophoresis) gels followed by Coomassie blue staining (Diversified Biotech, Newton Centre, Mass.). The fractions containing greater than 70% antibody were pooled. The antibody was then chromatographed on an AVID-AL (Bioprobe International, Tustin, Calif.) column that has been prepared according to the manufacturer's specifications. After the antibody is chromatographed over the column, the column is washed with PBS. The bound material was eluted with 0.1M sodium acetate, pH 3.0. The pH of the fractions are neutralized by adding 1M TRIS-HCl, pH 8.0 to a final concentration of 100 mM. The peak fractions are pooled, dialyzed against PBS, and analyzed by pre-poured 12% SDS-PAGE or 12% TRIS/Glycine gels (BioRad, Richmond, Calif. or Novex, San Diego, Calif., respectively). The purity of the antibody was 95% or greater at this stage.

Figure 1B:
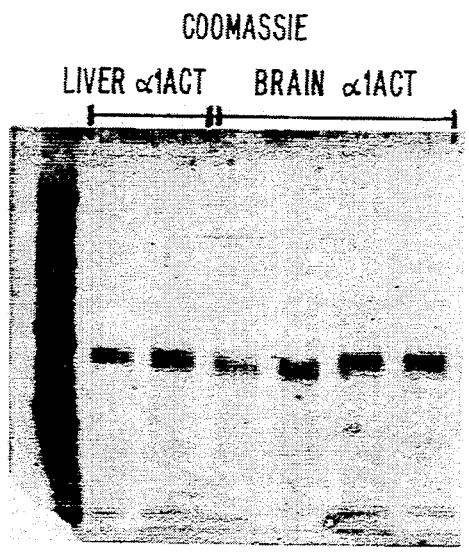
FIG. 1(b) is a Coomassie blue-stained SDS-PAGE gel indicating the presence of liver α1-ACT and brain α1-ACT in the gel used to make the immunoblot.

Immunoblot Analysis 7.5% SDS-PAGE pre-poured gels from BioRad were run at constant milliamps (12 mA/gel) and either stained with Coomassie stain or transferred onto Immobilon, a PVDF membrane (Millipore, Bedford, Mass.) in a wet transfer apparatus at constant volts in transfer buffer (10 mM 3-[cyclohexylamino]-1-propane-sulfonic acid (CAPS), 10% MeOH, 0.01% SDS, pH 11.0). The membrane is rinsed in TRIS-buffered saline (TBS; 20 mM TRIS-HCl, 5 mM TRIS-base, 137 mM NaCl, 5 mM KCl, pH 7.5), and placed into blocking reagent (catalog #1096 176; Boehringer Mannheim, Mannheim, Germany) at 0.5 g per 100 ml of TBS and incubated for 1 hour at 21° C. The membrane is washed two times for 10 minutes in TBS with a final 10 minute wash in TBS, 1.0 mM MgCl, 1.0 mM CaCl, 1.0 mM MnCl$_2$ (buffer 1). The lectin, *Aleuria aurantia* agglutinin (AAA) from Boehringer Mannheim labeled with biotin or digoxigenin (catalog #'s 1243 179 or 1243 187, respectively), is diluted 1:1000 (10 ug/ml) in buffer 1 and incubated with the membrane for 1 hour at 21° C. Once the labeled-AAA incubation is complete, the membrane is washed three times for 10 minutes with TBS, and then incubated with avidin-alkaline phosphatase (Boehringer Mannheim) at 1:1000 dilution or anti-digoxigenin-alkaline phosphatase (Boehringer Mannheim) at 1:1000 dilution whether the lectin was labeled with biotin or digoxigenin labeled lectins. The membrane is washed again in TBS three times for ten minutes. The membranes were developed using 4-nitroblue tetrazolium chloride (NBT) at 30 mg/ml in 70% (v/v) N,N-dimethylformamide (DMF) and 5-bromo-4-chloro-3-indolylphosphate (BCIP) at 15 mg/ml in DMF. The NBT and BCIP are diluted 1:100 in carbonate buffer (0.1M Na$_2$HCO$_3$, 1.0 mM MgCl$_2$, pH 9.8 prior to development. The membranes imaged with labeled-AAA are usually developed for 1–10 minutes before stopping the reaction by immersing the membrane in distilled H$_2$O. FIG. 1A illustrates the AAA lectin reactivity with brain α1-ACT and the absence of reactivity with liver α1-ACT by immunoblot analysis, and a Coomassie blue-stained gel shown in FIG. 1B demonstrates the quantity and quality of the purified liver α1-ACT and purified brain α1-ACT. The same procedure is followed when imaging the blots with antibodies except gelatin may be used instead of blocking reagent; Tween-20 at a final concentration of 0.05% is added to the buffers after the blocking step, and goat anti-mouse IgG-alkaline phosphatase (BioRad) or goat anti-rabbit-alkaline phosphatase (BioRad are used at 1:5000 when using mAbs or polyclonal antibodies (Abs), respectively. The development time can vary with mAbs or polyclonal depending on the Ab used.

Other lectins that were used in the analysis of the brain and liver forms of α1-ACT are: A3 (*Anguilla anguilla* agglutinin), Con A (Concanavalin A), DSA (*Datura stramonium* agglutinin), GNA (*Galanthus nivalis* agglutinin), LTL (*Lotus tetragonolobus* lectin), LCA (*Lens culinaris* agglutinin), MAA (*Maackia amurensis* aglutinin), PHA-L *Phaseolus vulgaris* leucoagglutinin), PNA (Peanut agglutinin), PSA (*Pisum sativum* agglutinin), RCA$_{120}$ (*Ricinus communis* agglutinin I), SNA (*Sambucus nigra* agglutinin), UEAI (Ulex europaeus agglutinin, type I), and WGA (wheat germ agglutinin). The lectins were labeled with either biotin or digoxigenin, and the primary sources of the lectins were from Boehringer Mannheim (Mannhein, Germany) or Vector Laboratories (Burlingame, Calif.). These lectins did not substantially differentiate between liver α1-ACT and brain α1-ACT.

Measurement of the Brain Form of α1-Antichymotrypsin

A sandwich assay format is used to quantitate the levels of brain α1-ACT in plasma and CSF. An α1-ACT mAb, 16D2, is used to "capture" (i.e., bind with, typically to form an immobilized complex with) α1-ACT and the AAA lectin that is specific for brain α1-ACT serves as the "reporter" in one embodiment of the assay. Prior to coating the α1-ACT mAb onto a microtiter plate, the mAb generally is oxidized. Since IgG derived from eukaryotic cells is typically composed of approximately about 3% carbohydrate, the carbohydrate is usually oxidized to prevent any cross-reactivity of the AAA lectin with the carbohydrate which may be present on IgG. The carbohydrate on the IgG is generally oxidized by adding sodium periodate (NaIO$_4$) at a final concentration of 5 mM to a 1–3 mg/ml concentration of the mAb. For complete oxidation of the carbohydrates on IgG, the mAb and NaIO$_4$ are incubated for about four hours at 4° C. The oxidation reaction is stopped by the addition of 10 mM glycerol followed by dialysis to PBS.

Figure 2:
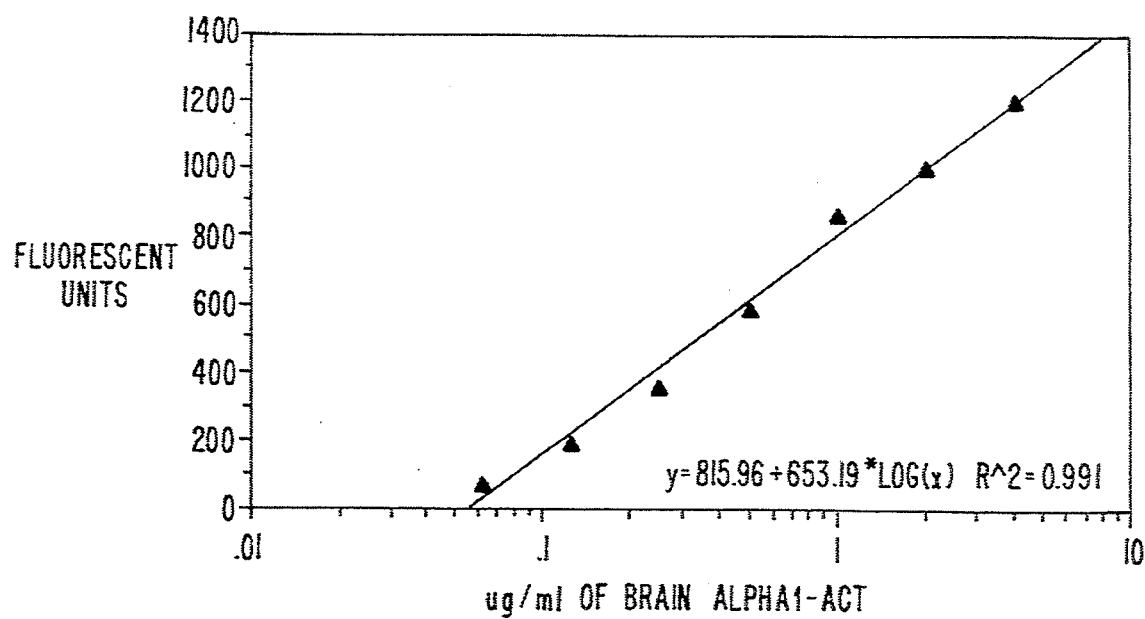
FIG. 2 is a standard curve of brain α1-ACT as measured in a brain α1-ACT immunoassay of the invention.

The oxidized mAb is coated at 10 ug/ml in carbonate buffer (0.1M Na$_2$HCO$_3$, 1.0 mM MgCl$_2$, pH 9.8) by adding 100 ul/well to a Costar (Cambridge, Mass.) 96-well microtiter plate (catalog #3590). The coating step is performed at 37° C. for two hours. At the end of this incubation, the plate is aspirated and 280 ul of 0.5% blocking reagent (catalog #1096 176; Boehringer Mannheim) in TBS is added to each well and incubated at 37° C for two hours. The plate is aspirated and washed three times with TBS, 0.05% Tween-20, pH 7.5. The standard or sample to be measured in the assay is diluted into assay dilution buffer (TBS, 0.02% blocking reagent, 0.05% Tween-20, pH 7.5) to the appropriate concentration and 100 ul is added per well. Again, the plate is incubated at 37° C. for two hours followed by the wash step described above. In the next step, a 50 nM concentration of biotinylated AAA lectin is made in TBS, 1 mM MgCl$_2$, 1 mM CaCl$_2$, 1 mM MnCl$_2$, 0.02% blocking reagent, 0.05% Tween-20, pH 7.5, and 100 ul is added per well. The lectin incubation step occurs at 21° C. for at least six hours or overnight. The plate is aspirated, washed and 100 ul of streptavidin-alkaline phosphate is added per well. The streptavidin-alkaline phosphatase (Boehringer Mannheim) is diluted 1:1000 into assay dilution buffer and incubated at 21° C. for one hour. After washing the plate, it is developed by adding 100 ul per well of 4-methylumbelliphenyl phosphate (Sigma) at 0.06 g/l in 0.35M 2-amino-2-methyl propanol buffer at pH 9.5. The plate is read on a Cytofluor 2350 Fluorescence Measurement System (Millipore) using a 365 nm excitation filter and a 450 nm emission filter for the substrate. FIG. 2 shows a standard curve from a brain α1-ACT sandwich assay.

Although the present invention has been described in some detail by way of illustration for purposes of clarity of understanding, it will be apparent that certain changes and modifications may be practiced within the scope of the claims.

---

We claim:

1. A method of detecting the presence or concentration of brain α1-antichymotrypsin in a sample from a patient comprising:

obtaining a sample of biological fluid or tissue from the patient;

contacting the sample with a binding component that specifically or preferentially binds to a carbohydrate component which is present in brain α1-antichymotrypsin but absent in other α1-antichymotrypsin isoforms;

detecting the presence or concentration of the brain α1-antichymotrypsin.

2. The method according to claim 1, wherein the step of contacting further comprises the steps of:

contacting the sample with a first binding component that binds to α1-antichymotrypsin isoforms; and contacting the bound α1-antichymotrypsin isoforms with a second binding component that binds brain α1-antichymotrypsin with a binding affinity that is at least 10-fold greater for brain α1-antichymotrypsin than for liver α1-antichymotrypsin.

3. The method according to claim 2, wherein the second binding component is a carbohydrate binding component.

4. The method according to claim 3, wherein the second binding component preferentially binds to complex N-linked glycan structures comprising carbohydrate residues selected from the group consisting of: $\alpha(1\rightarrow 6)$fucose and $\alpha(1\rightarrow 3)$fucose.

5. The method according to claim 3, wherein said second binding component is *Aleuria aurantia* agglutinin.

6. The method according to claim 3, wherein the second binding component preferentially binds to complex N-linked glycan structures that bind to *Aleuria aurantia* agglutinin with an affinity of at least about $1\times 10^6 M^{-1}$.

7. The method according to claim 2, wherein the first binding component is an antibody that binds to α1-antichymotrypsin isoforms.

8. The method according to claim 7, wherein the antibody is a monoclonal antibody.

9. The method according to claim 8, wherein the monoclonal antibody is selected from the group consisting of 7D7 and 16D2 having designations ATCC HB 11747 and ATCC HB 11748, respectively.

10. The method according to claim 1 wherein the binding component is a monoclonal antibody.

11. The method according to claim 1 wherein the contacting step comprises performing a sandwich immunoassay.

12. The method according to claim 11, wherein the sandwich immunoassay detects brain α1-antichymotrypsin captured in a complex consisting essentially of an antibody, brain α1-antichymotrypsin, and *Aleuria aurantia* agglutinin.

13. The method according to claim 12, wherein the antibody is immobilized on a solid support.

14. A method according to claim 1, wherein the sample is selected from the group consisting of serum, plasma, cerebrospinal fluid, and brain tissue.

15. The method according to claim 2, wherein the first binding component is an antibody that binds to α1-antichymotrypsin isoforms and the second binding component is *Aleuria aurantia* agglutinin.

16. The method according to claim 15, wherein the *Aleuria aurantia* agglutinin is labeled.

17. A sandwich immunoassay for detecting a brain α1-antichymotrypsin in a biological fluid or tissue sample, comprising the steps of:

contacting the sample with a predetermined amount of a α1-ACT binding component and a carbohydrate binding component in a binding reaction under suitable binding conditions;

incubating the binding reaction to form bound complexes consisting essentially of said α1-ACT binding component, said brain α1-antichymotrypsin, and said carbohydrate binding component; and detecting said bound complexes in the binding reaction.

18. The sandwich immunoassay according to claim 17, wherein the carbohydrate binding component preferentially binds to $\alpha(1\rightarrow 6)$-fucose residues on complex N-linked glycan structures.

19. The sandwich immunoassay according to claim 18, wherein the carbohydrate binding component is *Aleuria aurantia* agglutinin.

20. The sandwich immunoassay according to claim 17, wherein the carbohydrate binding component contains a detectable label.

21. The sandwich immunoassay according to claim 17, wherein the α1-antichymotrypsin binding component contains a detectable label.

22. The sandwich immunoassay according to claim 17, wherein the α1-ACT binding component comprises an antibody.

23. The sandwich immunoassay according to claim 22, wherein the α1-ACT binding component comprises a monoclonal antibody.

24. The sandwich immunoassay according to claim 23, wherein the monoclonal antibody is selected from the group consisting of 7D7 and 16D2 having designations ATCC HB 11747 and ATCC HB 11748, respectively.

25. The sandwich immunoassay according to claim 17, wherein said bound complexes are insoluble in the binding reaction.

26. The sandwich immunoassay according to claim 22, wherein the antibody is immobilized.

* * * * *